United States Patent [19]

Valdiserri et al.

[11] 4,130,540
[45] Dec. 19, 1978

[54] OLEFIN POLYMERS STABLE TO COPPER

[75] Inventors: Leo L. Valdiserri, Belpre, Ohio; Elyse M. Bullock, Parkersburg, W. Va.

[73] Assignee: Borg-Warner Corporation, Chicago, Ill.

[21] Appl. No.: 854,860

[22] Filed: Nov. 25, 1977

[51] Int. Cl.² ............................................. C08K 5/51
[52] U.S. Cl. ....................... 260/45.8 R; 174/110 PM; 260/45.8 NE; 260/45.9 NP; 260/45.8 NZ; 260/45.85 B; 428/379
[58] Field of Search .............. 260/45.8 R, 937, 927 R, 260/45.9 NP; 428/379

[56] References Cited

U.S. PATENT DOCUMENTS

| 2,952,701 | 9/1960 | McConnell et al. | 260/927 R |
|---|---|---|---|
| 3,528,975 | 9/1970 | Pivawer et al. | 260/45.8 R |
| 3,535,257 | 10/1970 | Kutner | 260/45.75 W |
| 3,806,358 | 4/1974 | Glander et al. | 428/379 |
| 3,819,410 | 6/1974 | Kuckro et al. | 428/379 |
| 3,891,667 | 6/1975 | Lintzenich | 260/937 |
| 3,910,905 | 10/1975 | Dulog et al. | 260/927 R |
| 3,914,344 | 10/1975 | Schwarzenbach et al. | 260/937 |
| 3,923,733 | 12/1975 | Spector et al. | 260/45.9 NP |
| 3,997,505 | 12/1976 | Albright | 260/45.8 R |

Primary Examiner—Donald E. Czaja
Assistant Examiner—R. A. White
Attorney, Agent, or Firm—Joseph Shekleton

[57] ABSTRACT

Stabilization of olefin polymers against deterioration in the presence of copper. The stabilization is accomplished by means of a small proportion of a bis-phosphoramidate having the structure

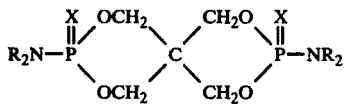

where the R's are inert, organic groups.

7 Claims, No Drawings

OLEFIN POLYMERS STABLE TO COPPER

BACKGROUND OF THE INVENTION

The invention of this application relates to the stabilization of olefin polymers in the presence of copper.

Olefin polymers have many desirable properties which qualify them for a wide variety of uses. Polypropylene, for example, is a tough, hard, relatively flexible, high-melting polymeric material. It is especially useful as electrical insulation for copper wires and cables. In certain respects, however, the stability of polypropylene is less than satisfactory. Its melt index decreases rapidly and it becomes brittle when kept at elevated temperatures for the time required in milling, calendering, extrusion, injection molding and fiber-forming equipment. This deterioration is particularly serious when the polymers are worked in this fashion in the molten state in an atmosphere of oxygen, i.e., in air. Many well-known antioxidants have been used to inhibit this kind of deterioration, including hindered phenols, secondary aromatic amines, organic phosphites and thiodipropionic acid esters.

The problem is somewhat complicated when the olefin polymer is contaminated by copper or is to be used in contact with copper. When used as insulation for copper wire or cable, for example, polypropylene deteriorates within a few months to the point at which it is virtually useless. As a matter of fact, even in the presence of anitoxidants such as those above, polypropylene degrades rapidly in the presence of copper.

The otherwise excellent mechanical and electical properties of olefin polymers point up the importance of efforts to find ways to prevent this thermal instability in the presence of copper.

U.S. Pat. No. 3,535,257 (Kutner) teaches the stabilization of olefin polymers against this type of deterioration by means of a combination of zinc sulfide, a phenolic antioxidant and a thiodialkanoic acid diester.

U.S. Pat. No. 3,549,572 (Minagawa et al.) teach the use of certain mercapto and thio hydrazides for the same purpose.

An article entitled "Electrical Wire and Cable Plastics Coating — What's Ahead?" by D. V. Rosato, on page 54 of Wire and Wire Products for March, 1970, teaches the use of ethylene/propylene copolymer instead of polypropylene to ameliorate this problem.

U.S. Pat. No. 3,978,167 (Albright) discloses the use of certain diphosphoramidates of pentaerythritol as flame retardants for synthetic polymers. bis(dialkylamino)-pentaerythritol diphosphates are among those disclosed and the bis(diethylamino)pentaerythritol diphosphate is specifically shown. (See Example 3 at column 7.)

The invention herein is an olefin polymer composition comprising a major proportion of an olefin polymer normally susceptible to deterioration at high temperatures in the presence of copper, and a minor proportion sufficient to inhibit such deterioration, of a bis-phosphoramidate having the structure

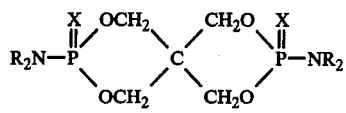

where R is the same or different inert, organic radical and X is oxygen or sulfur.

Such compositions are characterized by unexpected resistance to deterioration at high temperatures in the presence of copper and are, therefore, notably useful as insulation and coating for copper wire.

The olefin polymer may be either a homopolymer or copolymer, but, if the latter, it should comprise at least about 90% of olefin units. Polymers contemplated include polyethylene (low density and high density), polypropylene, polyisobutylene, EPDM polymers, copolymers of ethylene and propylene, copolymers of ethylene and vinyl acetate, copolymers of propylene and vinyl acetate, copolymers of ethylene or propylene with up to 10% of a higher ($C_4$-$C_6$) monoolefin, and terpolymers of ethylene and propylene. The polymers of ethylene and propylene are preferred, and the copolymer of ethylene and propylene is especially preferred.

The bis-phosphoramidates may be prepared by reaction of dichloro pentaerythritol diphosphite with a dialkyl amine, for example, to form the intermediate bis-phosphormaidite. Then, this intermediate is oxidized to the desired bis-phosphoramidate. The following equations are illustrative:

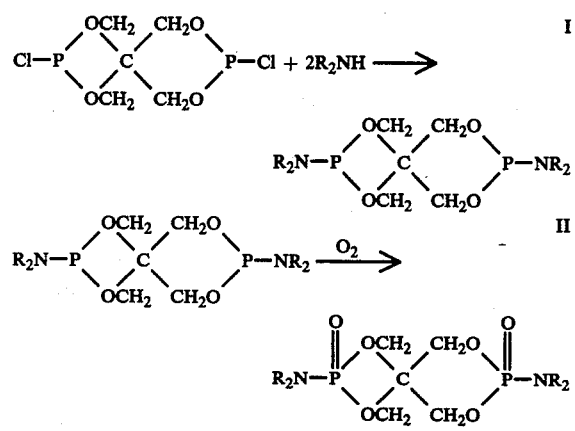

The bis-phosphoramidates herein are those in which R is the same or different alkyl, aryl, cycloalkyl or both R's taken with the nitrogen to which they are attached are one heterocyclic radical. Specific illustrative examples includes methyl, ethyl, propyl, butyl, hexyl, octyl, decyl, tetradecyl, phenyl, tolyl, naphthyl, cyclopentyl, cyclohexyl, methylcyclohexyl, morpholinyl, imidazolyl, piperidyl and the like. Preferred bis-phosphoramidates are prepared according to the above equation when the secondary amine reactant is a dialkyl amine, especially a lower dialkyl amine, i.e., one wherein the alkyl groups are each of 1-6 carbon atoms. The alkyl groups usually are alike although they may be unlike. In most instances, and preferably so, they are each methyl, i.e., the dialkyl amine is dimethyl amine. From about 0.1% to about 1.0% of the bis-phosphoramidate, based on the weight of the polymer composition, should be used, for best results.

Step I represented above may be carried out at a temperature within the range of from about 0° C. to about 120° C. Higher or lower temperatures can be employed, but higher temperatures afford no additional benefit to the reaction and lower temperatures require a longer reaction time. The reaction is exothermic. Generally, a solvent is used, such as benzene or toluene, and the reaction is carried out at the reflux temperature of the solvent.

The process by which Step I may be carried out is illustrated by the following examples:

EXAMPLE 1

Dimethyl amine (45.0 g., 1.0 mol) is bubbled into a solution of 62.2 g. (0.25 mol) of dichloro pentaerythritol in 200 ml. of benzene, over a period of one hour. The reaction is slightly exothermic and the temperature is controlled at 30°–40° C. The product mixture is filtered and the solid dimethylamine hydrochloride washed thoroughly with hot benzene to extract all of the desired bis-(dimethylamino) pentaerythritol phosphoramidite, and the benzene washings are added to the filtrate. The cooled benzene deposits a 70% (of the theory) yield of a colorless solid, M.P. 172°–176° C.

EXAMPLE 2

To a 332 g. (4.55 mols) of diethyl amine there is added, portion-wise, a solution of 265 g. (1.0 mol) of dichloro pentaerythritol diphosphite in 400 ml. of benzene. The temperature of the exothermic reaction is controlled at about 30°–40° C. by external cooling. The product mixture is stirred for about 16 hours after all of the benzene solution has been added and then it is filtered. The filtrate is concentrated, yielding 277 g. of a solid residue which is crystallized from heptane to yield 130 g. (38.5% of the theory) of bis-(diethylamino)pentaerythritol phosphoramidite, M.P. 83°–86° C.

EXAMPLE 3

To a solution of 16.6 g. (0.19 mol) of morpholine and 20 g. (0.2 mol) of triethyl amine in 100 ml. of benzene there is added, portionwise, a solution of 25 g. (0.09 mol) of dichloro pentaerythritol diphosphite in 100 ml. of benzene. The temperature of the resulting exothermic reaction is controlled at 40°–50° C. by external cooling. When the addition is complete the product mixture is heated and filtered. The cooled filtrate deposits 42 g. (60% of the theory) of white crystals, M.P. 182°–184° C.

EXAMPLE 4

To a mixture of 14.2 g. (0.2 mol) of pyrrolidine and 23.3 g. (0.23 mol) of triethyl amine there is added, portionwise, a solution of 26.5 g. (0.1 mol) of dichloro pentaerythritol diphosphite in 50 ml. of benzene. The resulting exothermic reaction is cooled externally so as to maintain the temperature at 40°–50° C. When all of the benzene solution is added the mixture is heated and then filtered. The cooled filtrate deposits 21.5 g. (64% of the theory) of a solid, M.P. 131°–133° C.

EXAMPLE 5

To a mixture of 13.6 g. (0.2 mol) of imidazole and 23.3 g. (0.23 mol) of dichloro pentaerythritol diphosphite in 50 ml. of benzene. The temperature of the resulting exothermic reaction is controlled at 40°–50° C. by external cooling. When the addition is complete, and the exothermic reaction has subsided, the reaction mixture is heated and filtered. The filter cake is washed with methylene chloride and the methylene chloride washing added to the filtrate and the whole is evaporated to a solid residue weighing 17.5 g. (53% of the theory), M.P. 125°–128° C.

The oxidation of the bis-phosphoramidites (Step II) prepared as in Examples 1–5 illustrated in the following examples:

EXAMPLE 6

To 19.5 g. (0.07 mol) of bis-(dimethylamino)pentaerythritol phosphoramidite (prepared as in Example 1) there is added, portionwise and with stirring, a solution of 16.5 g. (0.14 mol) of 29% aqueous hydrogen peroxide. The resulting exothermic reaction is cooled externally so as to maintain the temperature at 30°–40° C. When all of the hydrogen peroxide has been added, the mixture is stirred at room temperature for 30 minutes and then filtered. The solid bis-(dimethylamino)pentaerythritol phosphoramidate weighs 19.0 g. (90% of the theory) and melts with discoloration at about 260° C.

EXAMPLE 7

To a solution of 28.2 g. (0.1 mol) of bis-(dimethylamino)pentaerythritol diphosphite in 125 ml. of chlorobenzene, heated with stirring at 120° C., there is added, portionwise over a period of 20 minutes, 6.4 g. (0.19 mol) of sulfur. The resulting reaction is exothermic and the addition of the sulfur is timed so as to maintain the temperature at about 120° C. When all of the sulfur has been added the product mixture is allowed to cool and then filtered. The filter cake is washed with chlorobenzene and air-dried. It weighs 33 g. (95% of the theory) and melts at 245°–250° C. (blackens).

EXAMPLE 8

To a solution of 83.5 g. (0.71 mol) of 29% aqueous hydrogen peroxide and 9.4 g. (0.09 mol) of triethylamine in 390 ml. of isopropyl alcohol, at room temperature, there is added with stirring 130 g. (0.34 mol) of bis-(phenylamino)pentaerythritol phosphoramidite. The reaction which results is exothermic and the phosphoramidite is added in portions so as to keep the temperature at 30°–40° C. When all of the phosphoramidite has been added the product mixture is filtered yielding 46 g. (33% of the theory) of a white solid, M.P. 218°–219° C.

EXAMPLE 9

To a stirred solution of 63.8 g. (0.57 mol) of 29% aqueous hydrogen peroxide and 5.0 g. (0.05 mol) of triethyl amine in 200 ml. of acetone, at room temperature, there is added, portionwise, 89.0 g. (0.26 mol) of bis-(morpholinyl)pentaerythritol phosphoramidite (prepared as in Example 3). The temperature of the exothermic reaction is controlled at 30°–40° C. by the rate at which the diphosphite is added. When all is added, the product mixture is filtered and the solid, weighing 62 g. (64% of the theory), is crystallized from water. It does not melt at 290° C.

The compositions herein may also desirably contain a phenolic antioxidant. Those specifically contemplated contain the group

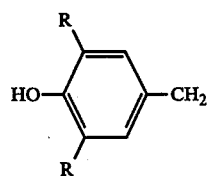

within their molecular structure. In the preferred instance R is tertiary butyl and especially preferred are those phenolic compounds which conform to the structure

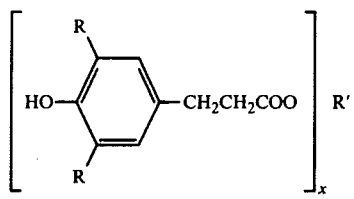

where R is tertiary butyl, R' is the residue of an alcohol or glycol, and x is 1–4 depending on the number of esterifying hydroxyl groups on the alcohol or glycol. From 0.05% to 0.5% should be used.

Other antioxidants contemplated for inclusion in these olefin polymer compositions include the thiodipropionate esters, i.e., $S(CH_2CH_2COOR)_2$ where R is alkyl of 8–20 carbon atoms. The distearyl ester is preferred. From 0.05% to 0.5% should be used.

Other polymer additives may also be used with the olefin polymer compositions herein including lubricants, heat and ultraviolet stabilizers, antistatic agents, flame retardants, plasticizers, etc.

The effectiveness of the compositions herein in stabilizing olefin polymers against deterioration in the presence of copper is shown by test data set out in the table below. The tests are carried out on 100-mil thick discs, 1 inch in diameter. A piece of fine copper gauze is imbedded in the copolymer of ethylene and propylene and 0.1 part of Irganox 1010.* The test sample illustrative of the invention also contains 0.4 part of the phosphoramidate product of Example 6.

*tetrakis[3-(3',5'-ditertiary-butyl-4'-hydroxyphenyl)propionate]methane.

TABLE

| Sample | Lifetime at 140° C |
|---|---|
| 1. Ethylene/propylene copolymer + Irganox 1010 | 639 hours |
| 2. Ethylene/propylene copolymer + Irganox 1010 + phosphoramidate product of Example 6 | 1326 hours |

We claim:

1. An olefin polymer composition in contact with a copper metal article, said composition comprising a major proportion of an olefin polymer normally susceptible to deterioration at high temperatures in the presence of copper, and a minor proportion sufficient to inhibit such deterioration, of a bis-phosphoramidate having the structure

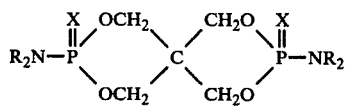

where R is the same or different alkyl, aryl or cycloalkyl or where both R's taken with the nitrogen to which they are attached are one heterocyclic radical and X is oxygen or sulfur.

2. The olefin polymer composition of claim 1 wherein R is in each case a lower alkyl group.

3. The olefin polymer composition of claim 1 wherein R is in each case methyl.

4. The olefin polymer composition of claim 1 wherein the olefin polymer is a polymer of an olefin containing 2–3 carbon atoms.

5. The olefin polymer composition of claim 1 wherein the olefin polymer is a copolymer of ethylene and propylene.

6. The olefin polymer composition of claim 1 wherein said composition contains also an effective amount of a phenolic antioxidant.

7. The olefin polymer composition of claim 6 wherein the phenolic antioxidant conforms to the structure.

* * * * *

UNITED STATES PATENT OFFICE
CERTIFICATE OF CORRECTION

PATENT NO. : 4,130,540
DATED : December 19, 1978
INVENTOR(S) : Leo L. Valdiserri and Elyse M. Bullock It is certified that error appears in the above-identified patent and that said Letters Patent are hereby corrected as shown below:

Column 6, line 40 cancel the period (.) after "structure" and add the following:

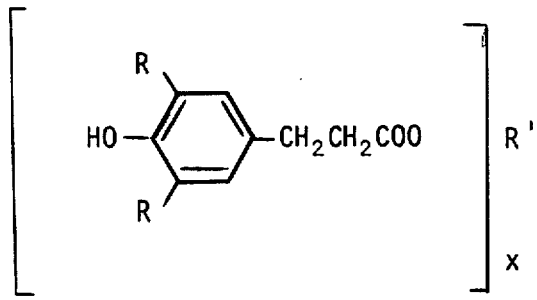

where R is tertiary butyl, R' is the residue of an alcohol or glycol, and x is 1-4.

Signed and Sealed this

Seventeenth Day of April 1979

[SEAL]

Attest:

RUTH C. MASON
Attesting Officer

DONALD W. BANNER
Commissioner of Patents and Trademarks